US008703467B2

(12) United States Patent
Reiter et al.

(10) Patent No.: US 8,703,467 B2
(45) Date of Patent: Apr. 22, 2014

(54) INACTIVATION OF A PATHOGEN IN A SAMPLE BY A TREATMENT WITH FORMALIN AND UV LIGHT

(75) Inventors: Manfred Reiter, Vienna (AT); Wolfgang Mundt, Vienna (AT); Noel Barrett, Klosterneuburg/Weidling (AT); Otfried Kistner, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 1553 days.

(21) Appl. No.: 11/138,158

(22) Filed: May 26, 2005

(65) Prior Publication Data

US 2006/0270017 A1 Nov. 30, 2006

Related U.S. Application Data

(60) Provisional application No. 60/575,310, filed on May 27, 2004.

(51) Int. Cl.
*C12N 7/04* (2006.01)
*C12N 7/06* (2006.01)

(52) U.S. Cl.
USPC ........................................ 435/235.1; 435/239

(58) Field of Classification Search
USPC .......................................... 435/5, 235.1, 239
See application file for complete search history.

(56) References Cited

U.S. PATENT DOCUMENTS

| | | | | |
|---|---|---|---|---|
| 2,725,482 | A | 11/1955 | Levinson et al. | |
| 3,259,547 | A | 7/1966 | Cole | |
| 3,926,556 | A | 12/1975 | Boucher | |
| 4,370,264 | A * | 1/1983 | Kotitschke et al. | 530/383 |
| 5,247,178 | A | 9/1993 | Ury et al. | |
| 2002/0096648 | A1 | 7/2002 | Kaiser et al. | |
| 2003/0108859 | A1 * | 6/2003 | Kistner et al. | 435/5 |

FOREIGN PATENT DOCUMENTS

| | | |
|---|---|---|
| GB | 802048 | 9/1958 |
| SU | 1367487 A1 | 10/1995 |

OTHER PUBLICATIONS

Benesi, E.; "Design of a Centrifugal Filmer for the Ultraviolet Irradiation of Liquids"; *General Motors Engineering Journal*; pp. 1-8 (Oct.-Dec. 1956).
Bokhnevich, G.M., et al.; "Effect of Ultraviolet Irradiation and Formalin on the Antigenic Properties of the Hemagglutinin and Neuraminidase from the Influenza A/Victoria/72 Virus"; *Trudy Insituta Imeni Pastera*; 47:24-31; English Translation, 8 pages (1976).
Coppey, J., et al.; "Enhanced Survival of U.V.-irradiated Herpes Virus in Monkey Kidney Cells Treated with Formaldehyde, Vinyl Chloride Monomer or X-rays"; *International Journal of Radiation Biology*; vol. 38; pp. 106-107 (1980).
Darnell, M.E.R, et al.; "Inactivation of the Coronavirus that Induces Severe Acute Respiratory Syndrome, SARS-CoV"; *Journal of Virological Methods*; vol. 121:1; pp. 85-91 (2004).
Goldstein, M.A., et al.; "Effect of Formalin, β-Propiolactone, Merthiolate, and Ultraviolet Light Upon Influenza Virus Infectivity, Chicken Cell Agglutination, Hemagglutination, and Antigenicity"; *Applied Microbiology*; vol. 19:2; pp. 290-294 (1970).
McLean, I.W., Jr., et al.; "Experiences in the Production of Poliovirus Vaccines"; *Virol.*; vol. 1; pp. 122-164 (1958).
Miyamae, T.; "Protective Effects of Nasal Immunization in Mice with Various Kinds of Inactivated Sendai Virus Vaccines"; *Microbiol. Immunol.*; vol. 30:3; pp. 213-223 (1986).
Molner, J.G., et al.; "A Study of the Serologic Response to Ultraviolet-Formalin Inactivated Poliomyelitis Vaccine"; *Am. J. Pub. Health*; vol. 48:5; pp. 590-598 (1958).
Taylor, A.R., et al.; "Inactivation of Poliomyelitis Virus for the Preparation of Vaccines"; *J. Immunol.*; vol. 79; pp. 265-275 (1957).
Truffelli, G.T., "Inactivation of Adenovirus and Simian Virus 40 Tumorigenicity in Hamsters by Vaccine Processing Methods"; *Applied Microbiology*; vol. 15:3; pp. 516-527 (1967).
Tsukui, M., et al.; "Antibody Production in Rats Vaccinated with Inactivated Sendai Virus"; *Exp. Anim.*; vol. 30:3; pp. 275-281 (1981). (English Abstract).
Turner, G.S., et al.; "Inactivated Smallpox Vaccine—A Comparison of Inactivation Methods"; *J. Hygiene*; vol. 68:2; pp. 197-210 (1970).
Zasukhina, G.D., et al.; "Variability of Western Equine Encephalomyelitis Virus"; *Acta. Virol.*; vol. 11:1; pp. 13-19 (1967).

* cited by examiner

*Primary Examiner* — Ruth Davis
(74) *Attorney, Agent, or Firm* — Kilpatrick Townsend & Stockton LLP

(57) ABSTRACT

The present invention relates to a method for inactivating virus in a sample by treating a virus containing sample with an effective concentration of formalin and by treating the sample with an effective dose of UV light in a flow-through apparatus.

20 Claims, 3 Drawing Sheets

INACTIVATION OF A PATHOGEN IN A SAMPLE BY A TREATMENT WITH FORMALIN AND UV LIGHT

FIELD OF THE INVENTION

Figure 1:
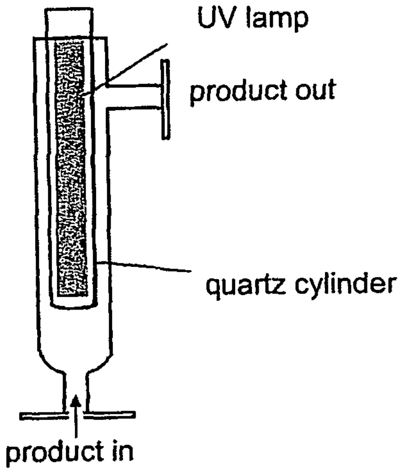

The present invention relates to a method for inactivating viruses by treating a virus containing sample with an effective concentration of formalin and by treating the sample with an effective dose of UV light in a flow-through apparatus.

BACKGROUND OF THE INVENTION

Effective inactivation of pathogens in medical products has been a public health concern since it was discovered that previously unknown diseases can be spread quickly through the administration of therapies. Therefore, biotechnological products are coming under increasingly stringent standards intended to decrease the risk of transmitting agents by their use. Potential contaminants not only are a problem in the manufacture of blood products but also in the production of safe vaccines.

One of the most critical steps in the production of vaccines against pathogens, in particular viral vaccines, is viral inactivation. In the case of virus inactivation, formalin is the most frequently used inactivating agent in the manufacture of vaccines. The formalin inactivation step has been validated with established analytical procedures. However, the introduction of highly stringent quality control tests such as mammalian cell culture tests, e.g., the Vero safety test, has demonstrated evidence of residual infectivity in some cases. In an effort to eliminate this residual infectivity mechanical disruption of aggregates and/or filtration turned out to be unsuccessful.

As an alternative to formalin treatment, UV inactivation has been considered for integration into the manufacturing process. The use of ultraviolet irridation-inactivation for human vaccines has been demonstrated before. Milzer et al. (Am. J. Pub. Health (1954) 44:26-33) and Wolf et al. (JAMA (1956) 161:775-81) have reported on immunogenicity results from studies in humans where they used UV inactivated poliomyelitis vaccine. Poliovirus is an unenveloped picornavirus, with a positive single stranded RNA genome in a single segment. As the viral genome is more susceptible to UV-damage than viral surface antigens, in the case of polio te viral capsid proteins, UV-inactivation was shown to have little negative effect on the biochemical characteristics or immunogenicity of the product. The targets for UV inactivation are primarily nucleic acids in contrast to proteins which are targeted by formalin. By combining formalin and UV-inactivation, scientists tried to overcome the limitations of isolated UV-inactivation or formalin-inactivation, respectively, when inactivating the particularly resilient poliovirus. See, e.g., McLean, et al., "Experiences in the Production of Poliovirus Vaccines," *Prog. Med. Virol.*, vol 1, pp. 122-164 (1958.)

UV radiation technologies have a broad application range in food, pharmaceutical, cosmetics and beverage industry, and drinking water. UV disinfection is a physico-chemical process, wherein covalent bonds of the cyclic molecules of the purine and pyrimidine bases are disrupted by the excitation energy of the UV wavelength radiation, damaging the nucleic acids and the genetic information that they encode. Microorganisms such as bacteria and yeasts, etc., as well as viruses that are exposed to effective UVC (100 to 280 nm) radiation are inactivated within seconds. Consequently, successful disinfection depends on the reduction-equivalent irradiation dose. The mean microbicidal irradiation dose expressed in $J/m^2$ is measured in the irradiation zone using a biodosimeter. However, UV-inactivation alone is not suitable for producing safe and effective vaccine.

Taylor et al. (J. Immunol. (1957) 79:265-75) describe the inactivation of poliomyelitis virus with a formalin and ultraviolet combination. Molner et al. (Am. J. Pub. Health (1958) 48:590-8) describe the formation of a measurable level of circulating antibodies in the blood of subjects vaccinated with ultraviolet-formalin inactivated polyomyelitis vaccine. Truffelli et al. (Appl. Microbiol. (1967) 15:516-27) report on the inactivation of Adenovirus and Simian Virus 40 Tumorigenicity in hamsters by a three stage inactivation process consisting of formalin, UV light and β-propiolactone. Miyamae (Microbiol. Immunol. (1986) 30:213-23) describes the preparation of immunogens of Sendai virus by a treatment with UV rays and formalin. None of the concepts described above has ever been adopted for general use in vaccine production, although there has been an ever-present need for the production of safe and efficacious vaccines on an industrial scale. In addition, none of the cited studies employed a safety test for determining the residual infectivity of the "inactivated viruses" that is as sensitive as the Vero safety test used in the present study.

Surprisingly, the inventors have found that a combination of formalin and UV inactivation steps can be utilized to fully inactivate virus in a bulk virus production in a high-volume throughput system for the manufacture of inactivated virus for vaccine preparation on an industrial scale. This has also been shown with a high-titer concentrated viral preparation as used in the examples, where no residual viral activity is detected using the very sensitive Vero cell culture test. The inventors have also surprisingly demonstrated that this method works particularly well for enveloped viruses, such as orthomyxoviruses, as compared to the unenveloped viruses, such as the polio picornavirus. This discovery has important implications for the rapid production of safe, highly immunogenic vaccines for emerging and rapidly changing viral diseases such as interpandemic and pandemic influenza strains.

SUMMARY OF THE INVENTION

It is an object of the present invention to provide a method which allows a highly efficient and safe inactivation of a virus contained in a sample while retaining a high antigenicity and immunogenicity of the inactivated virus. Particularly, the method of the present invention utilizes a formalin inactivation step in concert with a UV inactivation step in a high-volume throughput system to produce high-antigen content, safe bulk viral preparation for use in vaccine manufacture.

DETAILED DESCRIPTION OF THE INVENTION

According to one aspect of the invention, the object is solved by providing a method for inactivating a virus contained in a sample, comprising the steps of (i) treating the sample with an effective concentration of formalin, and (ii) subjecting the sample with an effective dose of UV light in a flow-through apparatus, wherein step (i) is performed prior to step (ii) or vice versa. Preferably, the flow rate of the sample through the apparatus is from about 50 liters per hour to about 1000 liters per hour.

In another preferred aspect of the method for inactivating the virus to be inactivated is an enveloped virus or an enveloped RNA virus, respectively, and the enveloped virus or the enveloped RNA virus, respectively, is wholly inactivated.

According to another aspect it is provided a method for inactivating a virus contained in a sample, comprising the steps of (i) treating the sample with an effective concentration of formalin, and (ii) subjecting the sample with an effective dose of UV light in a flow-through apparatus comprising a UV lamp and a thin layer chamber in the apparatus that is substantially perpendicular to the diameter of the UV lamp, wherein step (i) is performed prior to step (ii) or vice versa, wherein the sample is passed through the thin layer chamber of the apparatus in step (ii).

In a preferred embodiment of the invention the sample is treated with an effective dose of UV light in a flow-through apparatus after it has been treated with an effective concentration of formalin. Although the inventors are not bound by any theory, it is thought that the cross-linking effects of the formalin on the surface molecules of the virion stabilizes the virus for the rigors of the high-volume fluid dynamics of the UV inactivation flow-through apparatus.

The method of inactivating according to the invention is effective and safe as has been demonstrated in Example 2 and 4 (A). Moreover, the method of inactivating allows producing vaccines with high antigenicity and immunogenicity which elicit a protective immune response as shown in Example 4 (B).

The term "sample" as used herein includes any sample containing a pathogen or a part thereof such as any fluids, e.g. biological fluids or solutions originating from a cell culture process for preparing biological, medical, or pharmaceutical products such as blood products or vaccines. It may be a sample comprising a biological fluid, such as blood or plasma. It may also be a fluid containing harvested components of a cell culture (e.g., cell or culture media fraction of the culture). In a preferred embodiment the sample is a fluid used in the manufacture of a therapeutic agent e.g. in the production of a vaccine, in which the inactivated virus or a portion thereof is the therapeutic agent. In particularly preferred embodiments, cell components are separated from the sample prior to the inactivation method, for example by filtration or centrifugation.

In a preferred embodiment of the present application the virus is produced from a harvest of a cell culture, consisting of the supernatant and the cells, which is further used for the preparation of a medical product, e.g. a vaccine. In a further embodiment of the present invention the cells of said cell culture have been infected with the pathogen. The cells may be primary cells or any cultured cell line suitable for producing the virus. Examples of cells which may be used include mammalian cells (e.g., CHO, BHK, VERO, HELA cells), avian cells (e.g, chicken embryo fibroblasts, or continuous cell lines from an avian) and insect cells (e.g, Sf9 cells.) In preferred embodiments of the invention, the cells and cell debris from the cell culture production of the viral bulk are separated from the viral bulk prior to the chemical (formalin) inactivation step and/or the UV irradiation inactivation step.

In the present invention, the viruses to be inactivated are enveloped or unenveloped DNA or RNA viruses, with single or double (DNA) stranded genomes, sense or anitisense, continuous or segmented. The viruses may be selected from the group consisting of baculoviruses, poxviruses, adenoviruses, papovaviruses, parvoviruses, hepadnaviruses, coronaviruses, flaviviruses, togaviruses, astroviruses, picornaviruses, retroviruses, orthomyxoviruses, filoviruses, paramyxoviruses, rhabdoviruses, arenaviruses, and bunyaviruses. In preferred embodiments of the invention, the viruses are selected from the group of enveloped viruses, including, flaviviruses, togaviruses, retroviruses, coronaviruses, filoviruses, rhabdoviruses, bunyaviruses, orthomyxoviruses, paramyxoviruses, arenaviruses, hepadnaviruses, herpesviruses, and poxviruses. As demonstrated in Examples 6 and 7, the inactivation methods of the invention are particularly effective on enveloped viruses such as influenza and Ross River viruses, as compared to unenveloped polio and adenoviruses. In other preferred embodiments of the invention, the viruses are selected from the group of enveloped RNA viruses, including, flaviviruses, togaviruses, retroviruses, coronaviruses, filoviruses, rhabdoviruses, bunyaviruses, orthomyxoviruses, paramyxoviruses, and arenaviruses. In one particularly preferred embodiment, the virus is selected from the orthomyxoviruses, for example, an influenza virus strain: influenza virus strains may have varying combinations of hemaglutianin and neuraminidase surface proteins. In another particularly preferred example, the virus is selected from the togaviruses, for example an alphavirus such as the Ross River Virus (RRV.) Another preferred group of viruses for use as the bulk viral solution are the coronaviruses, including the virus associated with Severe Acute Respiratory Syndrome (SARS). Another group of preferred viruses are the flaviviruses, including Japanese Encephalitis, tick borne encephalitis (TBE), Dengue fever virus, yellow fevers virus, and hemorrhagic fever virus. Another preferred group of viruses are the poxviruses, including orthopoxviruses (such as vaccinia or modified vaccinia Ankara viruses), and avipoxviruses.

Parts of an inactivated viral pathogen are also encompassed by the present invention. In a preferred embodiment of the present application said parts can serve as an epitope in an immunogen. This epitope may be used to elicit an immune response against the pathogen. In a preferred embodiment of the present application parts of a pathogen are used as a vaccine against the pathogen. In an especially preferred embodiment said parts of a pathogen are split virions, which my be inactivated before or after being split.

Within the meaning of the present invention the method of inactivating according to the invention is considered safe, or wholly inactivated, when the inactivated virus produced using the method passes a mammalian cell culture test, for example, the safety test described in detail in Example 2. As demonstrated these tests are more sensitive than the other tests utilized, e.g, the egg test. Preferred pass/fail criteria of the safety test are detailed in Example 1 and 2.

In a preferred embodiment of the present application the virus titer reduction due to the inactivation of the virus in the sample is at least about $1\times10^5$, in a more preferred embodiment, at least about $1\times10^7$ in a more preferred embodiment at least about $1\times10^{10}$, and in a most preferred embodiment at least about $1\times10^{14}$.

In a preferred embodiment of the present invention, the sample is treated with an effective concentration of formalin for about 12 to about 96 hours. In more preferred embodiments, the sample is treated with an effective concentration of formalin for about 24 to about 48 hours, and more preferably for about 24 to about 30 hours.

In an especially preferred embodiment of the present invention, the sample is treated with an effective concentration of formalin for about 24 to about 24.5 hours.

In a further embodiment the step of treating the sample with an effective concentration of formalin is carried out at about 10 to about 40° C. In an especially preferred embodiment of the present application the step of treating the sample with an effective concentration of formalin is carried out at about 32° C.

A preferred embodiment of the present invention includes the treatment of the sample with an effective concentration of formalin, wherein the effective concentration of formalin ranges preferably from about 0.01% to about 1% (w/w), preferably from about 0.01% to about 0.1% more preferably between about 0.025% and about 0.1% which corresponds to about 92 mg/l and about 368 mg/l formalin respectively when using a 37% formalin solution for adjusting the effective concentration.

In the present application the term "UV light" means ultraviolet radiation having a wavelength of 100 to 400 nm. The UV light may be selected from the group consisting of UVC (100 to 280 nm), UVB (280 to 320 nm), and UVA (320 to 400 nm). Photosensitizing agents like those which intercalate into the DNA and are activated by UV light, e.g. psoralens, may be used to enhance the inactivating effect of the UV radiation. In a preferred embodiment of the present invention the UV light is UVC having a wavelength of about 100 to about 280 nm. In a more preferred embodiment of the present invention the UV light has a wavelength from about 240 to about 290 nm. In an especially preferred embodiment of the present invention about 85% or more of the UV light have a wavelength of about 254 nm.

The UV light emission may be a continuous form of UV light emission, e.g. mercury lamp technology, or pulsed UV light, e.g. monochromatic laser technology. The desired UV intensity may be generated by combining two or more lamps. In a preferred embodiment the UV light is emitted continuously by a lamp of about 110 W. In a preferred embodiment illustrated in the examples, the UV lamp has a length of about one meter, as does the lamp used in the examples (950 mm.)

The subject matter of the invention encompasses any effective dose of UV light, i.e. any dose of UV light which safely inactivates a given virus when combined with a formalin treatment as described above. The effective dose may depend on a variety of factors which are generally known in the field, e.g. the physical parameters of the UV inactivation chambers such as size and diameter of the lamp and the chamber, distance between the virus containing medium and the UV light source, light absorption and reflection properties of the material of the chamber. By the same token, the wavelength and intensity of the UVC light as well as the contact time the virus is exposed to the UV light is also critical for the effective dose. Furthermore, the effective dose is also influenced by the virus itself, the medium containing the virus and their light absorption properties. Preferably, the effective dose is sufficient for killing at least 99.99% of virus contained in the sample, more preferably inactivating the virus to a level where no active virus is detected in a mammalian cell culture test, preferably the test according to Example 2, or wholly inactivated. In a preferred embodiment using UVC light a sample containing the virus is exposed to an effective dose ranging from about 5 to about 200 $mJ/cm^2$. In a preferred embodiment the effective dose is in the range of about 20 to about 100 $mJ/cm^2$, and in other preferred embodiments the effective dose in the range of about 40 to about 90 $mJ/cm^2$. As a comparison, the effective dose for killing 99.99% of pathogens present in drinking water is about ≥40 $mJ/cm^2$. In a preferred embodiment, the effective dose reduces an initial virus titer by $1\times10^5$. In bulk vaccine inactivation, the effective dose should be sufficient to eliminate any residual live virus which may be present after the initial chemical (formalin) inactivation step. As illustrated in the examples, this may be determined by very sensitive mammalian cell culture infection tests, such as the Vero cell culture test described.

Further preferred embodiments of the invention and in particular of the UV light chamber are provided in the examples.

In a further preferred embodiment of the present invention the contact time of the sample with the UV light is in the range of about 1 to about 20 seconds, preferably from about 1.4 to about 14 seconds. The contact time is preferably calculated based on a sample which is approximately 1 mm thick along the tangent to the light source, and the wattage of the UV lamp of about 110 W. As one of skill in the art will appreciate, thicker sample depths and lesser energy (wattage) light sources would increase the exposure time and vice versa. In a more preferred embodiment of the present application the contact time of the sample with the UV light is about 1.4 to about 7 seconds and in an especially preferred embodiment of the present application the contact time of the sample with the UV light is about 2.8 to about 4.2 seconds.

In order to test whether a given set-up of the method according to the invention employing a given UV light dose effectively inactivates a pathogen according to the invention, one should test the inactivated virus for residual viral activity. This may be accomplished by using a mammalian cell culture test, for example the Vero safety test preferably applying the criteria detailed in Examples 1 and 2.

According to the present invention the treatment of the sample with an effective dose of UV light is carried out in a flow-through apparatus, preferably as specified in Table 1 and FIG. 1.

In a preferred embodiment of the present invention the flow-through apparatus contains a thin layer chamber. The minimum thickness of the chamber should allow sufficient flow of the bulk viral solution to allow for reasonable swift processing, and to prevent the disruption of virus for whole inactivated virus vaccines. Thus, preferably, the thin layer is at least about 0.1 mm thick for the production of whole inactivated virus. Also, due to the absorbance of the UV radiation by the bulk viral solution, and the need to ensure sufficient irradiation of all virus in the solution, the maximum thickness should not allow any virion to pass through the apparatus without being sufficiently irradiated. Thus, the thin layer should not be thicker than about 1 cm thick. The thin layer is preferably from 0.5 mm to 3 mm thick, and more preferably about 1 mm so that the maximum distance between the UV lamp and the pathogen to be inactivated is less than about 1 mm. Alternatively, the sample may be passed through the lamp parallel to the length of the lamp, so that the sample is irradiated from the outer diameter, rather than the inner diameter, of the sample chamber. Similarly, a lamp within a sample chamber within a lamp (or circle of lamps) could be used as a configuration, irradiating the sample chamber from both the internal and external diameters. In addition, the chamber is preferably designed so that the flow of the sample through the chamber is not strictly laminar, but rather is turbid. This will assist in mixing the virus through the sample medium, ensuring even exposure to the UV radiation.

In another preferred embodiment of the present application the flow-through apparatus contains an UV inactivation chamber, wherein the UV lamp has a diameter of about 30 mm and the chamber surrounding the UV lamp through which the sample flows has a diameter of about 32 mm. In a preferred embodiment of the present application the chamber has a total volume of about 92 ml.

The sample to be irradiated can be passed through the apparatus. In a preferred embodiment the sample is cooled while passing the UV irradiation chamber. In a further preferred embodiment of the present invention the sample passing the UV irradiation chamber has a temperature of about 2 to about 32° C., more preferably of about 2 to about 8° C.

Preferably, the flow-rate of the sample in the flow-through apparatus is in the range from about 50 to about 1000 liters per hour, more preferably about 230 to about 480 liters. In an especially preferred embodiment flow-rate of the sample in the flow-apparatus is in the range from about 230 to about 250 liters per hour, more preferably about 240 liters per hour.

These preferred flow rates, exemplified in the examples, allow for the economical large scale UV processing of the bulk viral solution.

In a preferred embodiment, the contact time depends on the length of the sample chamber in which the sample is exposed to the UV radiation, and the flow rate of the sample through the chamber. Thus, the effective dose which can be simply adjusted by increasing the number of UV-lamps arranged in the flow-through apparatus, increasing the effective length of the sample chamber exposed to UV radiation. Alternatively, using a same number of longer lamp-chambers will increase the effective dose, as using a larger number of shorter lamp-chambers may be equivalent to the same effective dose.

In a further preferred embodiment of the present application the step of subjecting the sample to an effective dose of UV light in a flow-through apparatus is repeated in a cyclic or serial manner. It may be repeated for about 2 to about 10 times. In a preferred embodiment of the present application the step of subjecting the sample to an effective dose of UV light in a flow-through apparatus is repeated for about 2 to about 5 times and in a more preferred embodiment of the present application it is repeated for about 2 to about 3 times. An added benefit to using multiple lamp chambers in serial, or recirculated flow through the same lamp, is that the sample may be more thoroughly mixed between chambers or cycles to ensure even exposure of the virus to the UV radiation.

After the virus in the sample has been inactivated, the inactivated virus may then be purified for use in various applications, including vaccine and other pharmaceutical compositions. According to another preferred embodiment of the invention, the method of inactivation further comprises a step of purifying the inactivated virus in the sample to pharmaceutical purity and formulating the purified virus into a pharmaceutical composition for used as a vaccine. Purification may be accomplished by means known in the art, including, but not limited to, filtration or diafiltration, chromatography (e.g., size exclusion, ion exchange, immunoaffinity, and the like,) or centrifugation. Alternatively, the virus may be purified prior to inactivation by the methods of the invention.

According to another preferred embodiment of the invention, the method of inactivation further comprises a purification step, i.e the sample is subjected to a purification step to remove residual formalin in the sample. Such purification is useful if levels of formalin remain which are higher than pharmaceutically acceptable levels. The inactivated virus, after optional purification steps, may then be formulated into a pharmaceutical composition. Formulations may optionally include carriers (e.g., physiological saline or buffers), excipients, stabilizers (e.g., albumin, saccharides, and/or amino acids,) salts, and/or adjuvants (e.g., alum). Alternatively, the inactivated virus may be further modified for pharmaceutical use, e.g., by encapsulation in liposomes.

The present invention will be further illustrated in the following examples, without any limitation thereto. Having described the invention in detail, it will be apparent that modifications and variations are possible without departing the scope of the invention defined in the appended claims.

FIGURES

FIG. 1 shows an UV thin layer chamber which may be used for the UV inactivation step of the present invention.

Figure 2:
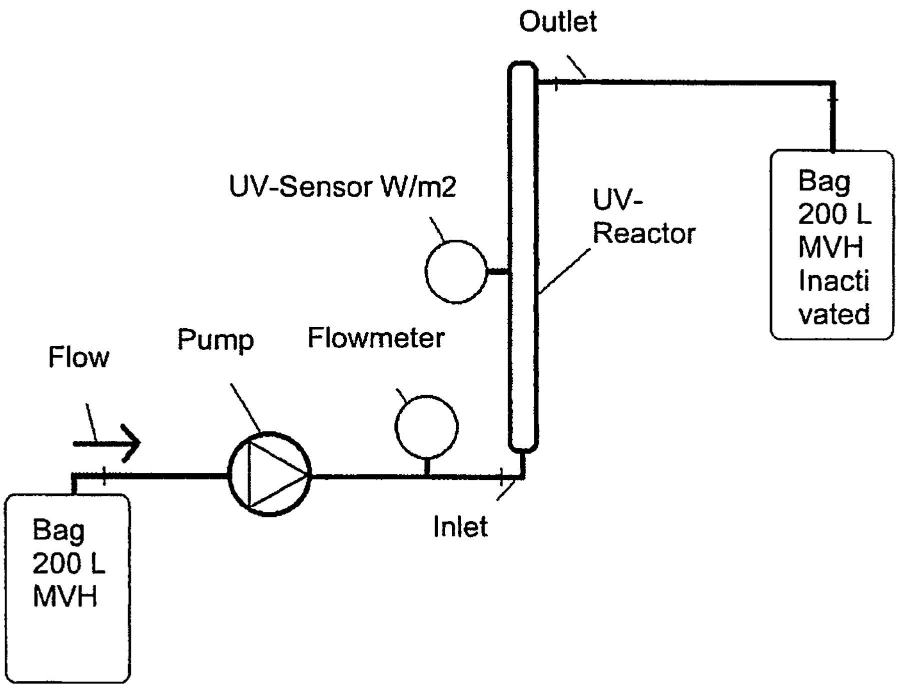

FIG. 2 shows an UV inactivation system equipped with an UV sensor. The UV sensor and flowmeter are optional features. In a further embodiment of the present application the pump and/or the flowmeter may be installed at the outlet tube.

Figure 3:
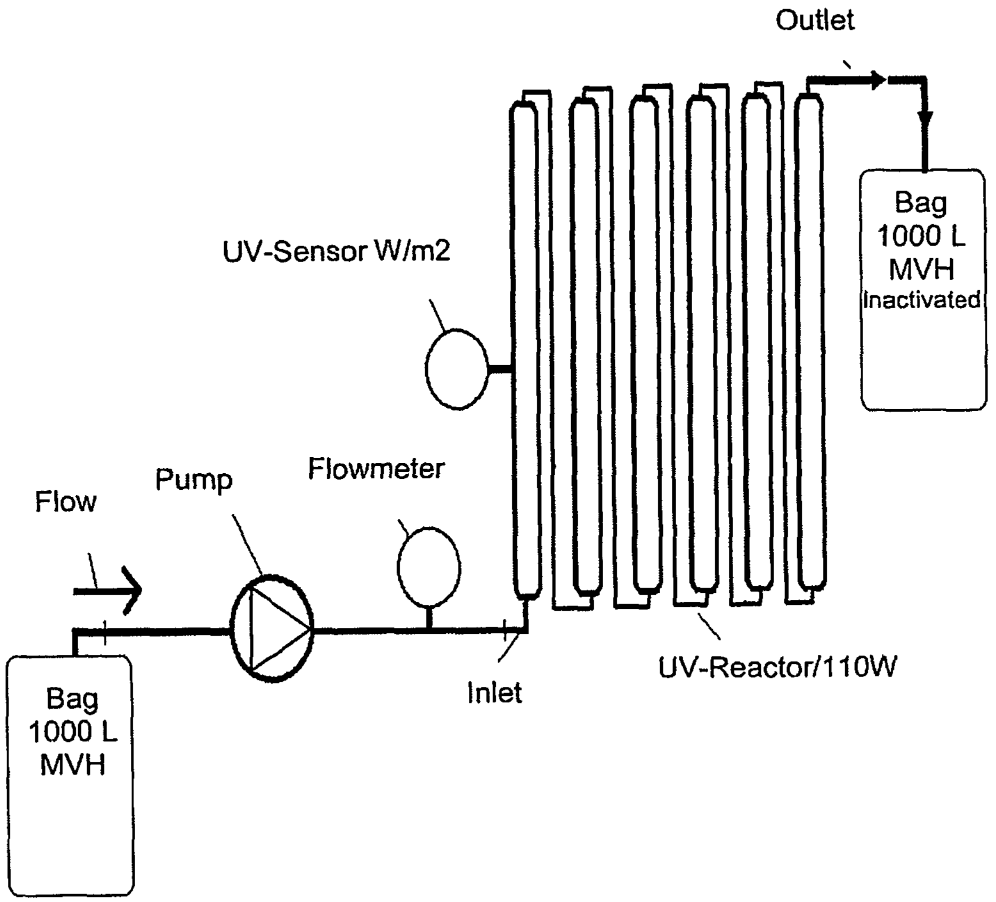

FIG. 3 shows an UV inactivation system utilizing several UV thin layer chambers (UV reactor) connected to each other for the repeated subjecting of the sample to an effective dose of UV light in a flow-through apparatus. The number of UV thin layer chambers may vary between about 2 and about 10. The UV sensor and flowmeter are optional features. In a further embodiment of the present application the pump and/or the flowmeter may be installed at the outlet tube. A continuous UV generator with serially connected inactivation chambers may be used in a large scale manufacturing process, thus allowing high throughput of a sample.

EXAMPLES

Example 1

Principle of the Standard Egg Safety Test

A standard egg safety test was used to test for residual infectivity of inactivated influenza strains. A monovalent bulk product, i.e. a purified virus antigen after sucrose gradient centrifugation and ultra-diafiltration, is injected into 10 eggs (0.2 ml/egg). After incubating for 3 days at 32° C., the eggs are harvested, pooled, and again injected into 10 eggs (0.2 ml/egg). After another incubation step for 3 days at 32° C., the eggs are harvested, pooled, and tested for hemagglutinin (HA).

The HA-test is based on the fact that Influenza viruses can bind erythrocytes using their surface protein hemagglutinin. The test is carried out in a sterile environment. A suspension of Influenza viruses with a defined HA titer serves as a positive control and a 0.9% NaCl solution serves as a negative control. 50 μl of a 1:2 dilution in 0.9% NaCl of a sample to be tested are given into one well of a 96-well plate. To each well 50 μl of a solution containing chicken erythrocytes is added. Subsequently, the plates are incubated for 30 to 45 minutes at room temperature. Then the hemagglutination is visually determined, wherein, if five wells containing the same sample do not show any hemagglutination, the sample passed the HA test.

Example 2

Principle of the Standard Vero Safety Test

The standard Vero safety test is a highly stringent quality test for the residual infectivity of inactivated influenza strains. The test is also applicable to other viruses. A monovalent bulk product, i.e. purified virus antigen after sucrose gradient centrifugation and ultra-diafiltration, is added to 5 Roux flasks (4 ml/flask). After incubating for 7 days at 32° C. in Vero culture medium, the cell cultures are harvested, pooled and added to 5 Roux flasks (10 ml/flask). After another incubation step for 7 days at 32° C., the cell cultures are harvested, pooled, and tested for hemagglutinin (HA) as described in Example 1.

Example 3

Formalin Inactivation

The first inactivation step with formalin is carried out on a cell-free, infectious monovalent virus harvest, i.e. a bioreactor harvest after clarification via centrifugation. After the collection at 30 to 34° C. the monovalent virus harvest is treated with about 0.9 to about 1.1 U/ml Benzonase at 30 to 34° C. for 4 to 8 hours. Then it is treated with ≤92 mg/l formalin for 24 to 24.5 hours at 32±2 hours.

Example 4

Inactivation Experiments with a 65 Watt UV Lamp

A number of inactivation experiments with formalin-inactivated viruses are carried out using an inactivation chamber with a 65 W UV lamp and a thin layer chamber. Although full inactivation of monovalent virus harvest can be demonstrated when using flow rates of 100 liter per hour for three cycles, this setup did not allow the on-line measurement of the UV signal. The Vero cell culture medium used for Influenza production contains various organic compounds being responsible for absorption of the UV signal. Therefore, the system, is equipped with a 110 W lamp allowing a continuous monitoring of the UV signal during monovalent virus harvest treatment.

Example 5

Inactivation Experiments with a 110 Watt UV Lamp

Formalin treated monovalent Influenza Panama harvest is used as a model substrate for the inactivation studies. For continuous inactivation with thin layer UV technology a WEDECO VISA system (Germany) equipped with a VISA lamp (110 W/4 V) is used. The UV thin layer chamber is a stainless steel 1.4435 device with a 30 mm diameter quartz tube (cf. Table 1). A calibrated UV sensor allows on-line control of the UV signal. The UV thin layer chamber is operated at a flow rate of 240±10 liter per hour at ambient temperature. The flow rate conditions are controlled by a calibrated flowmeter (cf. FIG. 2).

TABLE 1

Characteristics of the UV inactivation chamber.

| | |
|---|---|
| UV lamp | 110 W |
| length of lamp | 950 mm |
| Ø UV lamp | 30 mm |
| Ø chamber surrounding the UV lamp | 32 mm |
| thin layer | 1 mm |
| total volume/chamber | 92 ml |
| contact time/chamber | 1.4 seconds |

The monovalent harvest is exposed to 10 UV cycles. After each cycle 20 liter of the UV treated monovalent harvest is removed and further purified by sucrose gradient purification using continuous ultracentrifugation conditions with an extended 42% sucrose gradient in 20 mM Tris-buffer and a defined purified monovalent harvest (PMVH) from 48% to 36% sucrose using a Sorvall CC40 centrifuge without pre-clarifier (Hitachi Koki Co, LTD., Tokyo, Japan).

TABLE 2

Overview of ultracentrifugation runs of formalin and UV treated Influenza Panama.

| Ultracentrifugation Run | Inactivation Conditions |
|---|---|
| UZ-INF-45-03 | no UV |
| UZ-INF-48-03 | 240 l/hour, 1 cycle |
| UZ-INF-52-03 | 240 l/hour, 2 cycles |
| UZ-INF-51-03 | 240 l/hour, 3 cycles |
| UZ-INF-50-03 | 240 l/hour, 4 cycles |
| UZ-INF-49-03 | 240 l/hour, 5 cycles |

TABLE 2-continued

Overview of ultracentrifugation runs of formalin and UV treated Influenza Panama.

| Ultracentrifugation Run | Inactivation Conditions |
|---|---|
| UZ-INF-58-03 | 240 l/hour, 7 cycles |
| UZ-INF-57-03 | 240 l/hour, 10 cycles |

(A) Antigen Yield and Purity

Influenza antigen yield and purity are compared based on hemagglutinin content (HA), total protein and Vero-protein (host cell protein). The purified virus is compared on the basis of the HA/protein ratio, host cell protein/HA ration and virus safety (cf. Table 3). For all UV treated harvests no viral growth can be detected. In contrast, purified virus derived from standard formalin inactivation process (no UV radiation applied) can be amplified in Vero cell culture. Although a slight reduction in the HA/protein ratio can be seen after cycle 7 and 10, no significant difference of formalin and double inactivated product is detected with respect to antigen purity measured as HA/protein and host cell protein/HA ratio.

TABLE 3

Sucrose gradient purified Panama virus after formalin and UV treatment. Comparison of HA/protein ratio, host cell protein/HA ratio and safety after 0 to 10 UV cycles.

| Number of UV Cycles | Contact Time (s) | HA/ Protein ratio | Host cell protein/ HA ratio | Vero safety |
|---|---|---|---|---|
| 0 | 0 (no UV) | 0.85 | 0.04 | failed |
| 1 | 1.4 | 1.09 | 0.04 | passed |
| 2 | 2.8 | 0.88 | 0.04 | passed |
| 3 | 4.2 | 0.91 | 0.04 | passed |
| 5 | 7.0 | 0.83 | 0.04 | passed |
| 7 | 9.8 | 0.60 | 0.02 | passed |
| 10 | 14 | 0.58 | 0.03 | passed |

Further studies are carried out to characterize the effect of UV inactivation on antigenicity and immunogenicity in guinea pigs and mice by hemagglutinin inhibition (HAI) analysis.

(B) Antigenicity

Antigenicity is analysed by HAI assay against Panama specific antisera. Although increased UV contact time results in slight loss of HA, no negative effect is shown for the HAI titer (cf. Table 4).

TABLE 4

Sucrose gradient purified Panama virus after formalin and UV treatment. Comparison of antigenicity based on HA and HAI titer with Panama specific antisera after 0 to 10 UV cycles.

| Number of UV Cycles | Contact Time (s) | HA (μg/ml) | HAI titer |
|---|---|---|---|
| 0 | 0 (no UV) | 211 | 640 |
| 1 | 1.4 | 209 | 640 |
| 2 | 2.8 | 200 | 640 |
| 3 | 4.2 | 196 | 640 |
| 5 | 7.0 | 191 | 640 |
| 7 | 9.8 | 177 | 640 |
| 10 | 14 | 154 | 640 |

(C) Immunogenicity

Immunogenicity is analysed by immunizing guinea pigs and mice with different aliquots of the Purified Monovalent Virus Harvests followed by a booster three weeks after the first immunization. The sera of the immunized animals are collected and pooled after three and six weeks and analysed by HAI assay against egg-derived and Vero-derived antigens. Immunogenicity tested in guinea pigs and mice after 3 and 6 weeks give very promising results, no significant difference can be seen for the double inactivated virus versus standard formalin treated virus (cf. Table 5).

TABLE 5

Sucrose gradient purified Panama virus after formalin and UV treatment (0 to 10 cycles). Comparison of the immunogenicity tested in guinea pigs and mice. A) after 3 weeks, B) after 6 weeks. HAI with egg- and Vero-derived Influenza antigen.

A

| Number of | Contact | Guinea pigs HAI titer after 3 weeks | | Mice HAI titer after 3 weeks | |
|---|---|---|---|---|---|
| UV Cycles | Time (s) | Egg | Vero | Egg | Vero |
| 0 | 0 (no UV) | 160 | 320 | 320 | 1280 |
| 1 | 1.4 | 160 | 320 | 320 | 1280 |
| 2 | 2.8 | 160 | 640 | 320 | 1280 |
| 3 | 4.2 | 160 | 320 | 320 | 1280 |
| 5 | 7.0 | 160 | 320 | 320 | 1280 |
| 7 | 9.8 | 160 | 320 | 320 | 1280 |
| 10 | 14 | 160 | 640 | 320 | 1280 |
| control | — | 40 | 20 | 80 | 80 |

B

| Number of | Contact | Guinea pigs HAI titer after 6 weeks (Booster) | | Mice HAI titer after 6 weeks (Booster) | |
|---|---|---|---|---|---|
| UV Cycles | Time (s) | Egg | Vero | Egg | Vero |
| 0 | 0 (no UV) | 1280 | 1280 | 1280 | 2560 |
| 1 | 1.4 | 1280 | 2560 | 640 | 1280 |
| 2 | 2.8 | 1280 | 1280 | 640 | 1280 |
| 3 | 4.2 | 640 | 1280 | 1280 | 2560 |
| 5 | 7.0 | 1280 | 2560 | 1280 | 2560 |
| 7 | 9.8 | 640 | 1280 | 1280 | 2560 |
| 10 | 14 | 1280 | 2560 | 1280 | 2560 |
| control | — | 160 | 80 | 160 | 40 |

The results summarized in Table 4 and Table 5 show that the UV treatment does not result in significant differences in HAI titers demonstrating that the antigenicity and thus immunogenicity of the product is not affected.

In all double inactivation experiments total safety can be demonstrated even after 1 cycle of UV treatment. The detailed investigations in laboratory and final scale demonstrated the effectiveness of the UV irradiation step when combined with formalin treatment. The immunological characterization of the purified virus antigen after UV treatment yields results comparable to those obtained with non UV untreated product. No negative effect on the biochemical characteristics nor immunogenicity of the viral product can be detected.

Example 6

Virus Titer Reduction with Formalin and/or UV Inactivation

The virus titer reduction by the combined treatment of the sample with an effective concentration of formalin and an effective concentration of UV light in a flow-through apparatus is tested with different viruses. The formalin inactivation was carried out at 32° C. for 24 hours with a final formalin concentration of 0.025% (w/v). The UV inactivation in the flow-through apparatus is carried out for 3 cycles at a flow rate of 240 l/hour. The contact time of the sample with the UV light per cycle is 1.4 seconds.

TABLE 6

Virus titer reduction with formalin and/or UV inactivation.

| Virus | Virus Type | Measured Virus Titer Reduction after Formalin Treatment (log reduction) | Measured Virus Titer Reduction after UV Treatment (log reduction) | Calculated Virus Titer Reduction after Formalin and UV Treatment (log reduction) |
|---|---|---|---|---|
| Influenza New Caledonia | A/H1N1/20/99 | ≥7.4 | ≥7.3 | ≥14.7 |
| Influenza Panama | A/H3N2/2007/99 | ≥8.4 | ≥6.7 | ≥15.1 |
| Influenza Shangdong | B/7/97 | ≥6.7 | ≥7.2 | ≥13.9 |
| Polio | Type 1 | 3.0 | 4.9 | 7.9 |
| Adeno | Type 5 | 3.1 | 2.5 | 5.6 |

The results show that by a combined formalin- and UV-treatment of viruses a drastic reduction of the respective virus titers is obtained.

Example 7

UV-Inactivation of a Ross River Virus (RRV) Candidate Vaccine

Ross River Virus (RRV) is a mosquito borne alphavirus which causes a disease in humans known as epidemic polyarthritis (EPA). Symptoms include arthritis, particularly in the knees and in the small joints of the hands and feet, often accompanied by fever, rash and other non-specific constitutional changes. Arthritis symptoms commonly last 30-40 weeks and 25% of patients still have residual symptoms 1 year after onset. It is endemic in Australia, with more than 8000 cases each year, and throughout the Pacific region. In 1979/80 epidemics of Ross River Virus infection also occurred in Fiji, Samoa, the Cook Islands and New Calcdonia. There is currently no vaccine existing.

(A) RRV Inoculation of Serum-Free Microcarrier Based 1200 Liter Vero Cell Fermenter Cultures and Formalin Inactivation 1200 liter fermenter cultures of microcarrier based serum-free Vero cells were inoculated with Ross River production virus. The cultures were incubated for 3 days at 37° C. Samples were drawn every day for titration. At day 3, when 100% of the cells were destroyed by CPE (cytopathic effect) virus was harvested. After separation of cell debris and microcarriers from the infectious virus harvest and a first filtration step (1.2 μm/0.2 μm), benzonase was added for degradation of nucleic acids (DNA/RNA). Formalin inactivation was carried out with 0.1% (w/v) formalin end concentration for eight days. A second and a third filtration step were carried out after two hours and 24 hours, respectively. Benzonase was added a second time at 24 hours for removal of residual nucleic acids. Samples were drawn for virus titration=tissue culture infectious dose 50 ($TCID_{50}$/ml) in Vero cells and safety tests on C6-36 cells and Vero cells according to Table 7.

One day after inoculation of a 1200 liter fermenter with RRV, a virus titer of log $TCID_{50}$/ml of 5.8 could be demonstrated, which rose to 7.8 (day 2), 8.1 (day 3 before harvest) and 8.0 after virus harvest. After separation, first filtration and benzonase addition, virus titers dropped to 7.5, 7.2, and 7.4, respectively. After formalin addition, titers were determined after removal of the cytotoxic formalin suspension by centrifugation and resuspension of the virus pellet (Table 7, column: $TCID_{50}$/ml TL 100). 15 minutes after formalin was added to the virus harvest, titers dropped dramatically to 1.6. 12 h after formalin inactivation, no more virus titer could be demonstrated.

24 hours after onset of formalin inactivation samples were submitted to safety tests on C6-36 cells and Vero cells. Whereas after 24 h and 26 h after inactivation 1 positive (CPE) and 4 negative samples could be demonstrated on Vero cells, 4 positive and 1 negative sample were obtained with the much more sensitive C6-36 cell line. From day 2 onwards, all samples were negative on Vero cells. The C6-36 cell line still showed CPE with 1 sample on days 2 and 3, and 4 negative samples, respectively. On days 4 and 5 all samples tested negative on C6-36 cells, but on days 6 and 7 one sample again showed CPE. After day 8 no more positive samples could be shown on neither Vero cells nor C6-36 cells.

TABLE 7

Safety Results of a Ross River Virus Harvest of a 1200 Liter Fermenter.

| Sample | $TCID_{50}$/ml | $TCID_{50}$/ml TL100 | Safety C6-36 | Safety Vero |
|---|---|---|---|---|
| Infection day 1 | 5.8 | n.d. | n.d. | n.d. |
| Infection day 2 | 7.8 | n.d. | n.d. | n.d. |
| Infection day 3 | 8.1 | n.d. | n.d. | n.d. |
| Harvest | 8.0 | n.d. | n.d. | n.d. |
| after Separator | 7.5 | n.d. | n.d. | n.d. |
| after 1. Filtration (1.2 μm/0.2 μm) | 7.2 | n.d. | n.d. | n.d. |
| after Benzonase addition | 7.4 | n.d. | n.d. | n.d. |
| Formalin 0 h (15 minutes) | n.d. | 1.6 | n.d. | n.d. |
| Formalin 1 h | n.d. | 1.4 | n.d. | n.d. |
| Formalin 2 h (before 2. filtration) | n.d. | 1.4 | n.d. | n.d. |
| Formalin 3 h (after 2. filtration) | n.d. | 1.7 | n.d. | n.d. |
| Formalin 6 h | n.d. | 1.1 | n.d. | n.d. |
| Formalin 12 h | n.d. | <0.2 | n.d. | n.d. |
| Formalin 18 h | n.d. | <0.2 | n.d. | n.d. |
| Formalin 24 h (before 3. filtr., before 2. Benzonase add.) | n.d. | <0.2 | 4 positive 1 negative | 1 positive 4 negative |
| Formalin 26 h (after 3. Filtr., after 2. Benzonase add.) | n.d. | <0.2 | 4 positive 1 negative | 1 positive 4 negative |
| Formalin day 2 | n.d. | <0.2 | 1 positive 4 negative | 5 negative |
| Formalin day 3 | n.d. | <0.2 | 1 positive 4 negative | 5 negative |
| Formalin day 4 | n.d. | <0.2 | 5 negative | 5 negative |
| Formalin day 5 | n.d. | <0.2 | 5 negative | 5 negative |
| Formalin day 6 | n.d. | <0.2 | 1 positive 4 negative | 5 negative |
| Formalin day 7 | n.d. | <0.2 | 1 positive 4 negative | 5 negative |
| Formalin day 8 | n.d. | <0.2 | 5 negative | 5 negative |

(B) Transfection and Infection Experiments with RRV RNA

The results of the above mentioned safety tests raised suspicion, that genomic RRV RNA might be released during the inactivation procedure. This in turn could lead to incorporation of genomic RRV RNA into the respective cells. Although benzonase treatment should lead to complete degradation of RNA, liposome formation or other mechanisms like masking of the genomic RRV RNA with protein debris, could explain the escape strategy of intact RNA.

RRV genomic RNA was isolated from gradient purified virions. Via RT-PCR the number of particle equivalents could be determined. In a first experiment (Table 8, No. 1) particle equivalents (genomic RNA) were diluted in tenfold steps in both transfection medium (i.e. transfection) and regular medium (i.e. infection). With both mixtures C6-36 cells and Vero cells were inoculated. After a medium exchange, cell cultures were incubated for several days. Samples of the respective supernatants were used for virus titration and HA determination. Infection experiments with genomic RNA were carried out several times (Table 8, No's. 1-5).

The transfection experiments showed positive results in $TCID_{50}$ on both C6-36 cells and Vero cells. Vero cell supernatants also exhibited HA-Titers. The infection of Vero cells with a high number of particle equivalents ($10^8$) showed a virus titer of 6.8 log $TCID_{50}$/ml and had an HA-titer of 128, but failed to infect C6-36 cells. Another infection experiment with genomic RRV RNA (No. 4) resulted in both infected C6-36 cells and Vero cells, with titers of 8.4 and 6.6 log $TCID_{50}$/ml, respectively. Infection attempts 2, 3 and 5 gave no positive results on Vero cells. Infection attempt No. 3 gave a low titer of 1.6 log $TCID_{50}$/ml on C6-36 cells.

Although not all attempts to infect cells with pure genomic RRV RNA showed positive results, it seems that genomic RNA at high concentrations is capable to infect cells randomly. All experiments using a liposomic transfection reagent showed positive results. Hence, protein masking of RNA or liposome formation mechanisms will explain the positive safety tests after formalin inactivation and benzonase degradation of free DNA/RNA in Table 7.

(C) UV-Inactivation of Infectious RRV

For the above mentioned considerations, small scale experiments were carried out to inactivate RRV by UV-irradiation. RRV PV supernatants were UV-irradiated for different amounts of time with two UV-intensities: 2.1 mW/cm$^2$ (samples 1-10) and 3.3 mW/cm$^2$ (samples 11-20). Subsequently, these samples were submitted to virus titration, antigen-titration (EIA) and the hemagglutination titer was determined. Samples, which were irradiated for more than 3 minutes (No's. 6-10 and 14-19), were also submitted to safety testing on C6-36 cells (Table 9).

Virus titers dropped after 10 minutes of UV-irradiation from 7.4 log $TCID_{50}$/ml (control, sample #1) to 1.5 log $TCID_{50}$/ml with both UV-intensities. Hemagglutination remained stable for 15 minutes at an UV-intensity of 2.1 mW/cm$^2$ with an HA-titer of 9, but dropped to 8 at an UV-intensity of 3.3 mW/cm$^2$. Antigen-titers (EIA) also remained stable for 15 minutes of irradiation, within a range between 640-1280. Safety tests, carried out with samples irradiated for 3 and 5 minutes at an UV-intensity of 2.1 mW/cm$^2$ (sample No's. 6 and 7), still showed CPE in cell culture and gave virus titers of 8.2 and 8.6 log $TCID_{50}$/ml, respectively. Safety tests, carried out with samples irradiated for 2, 3 and 5 minutes at the higher UV-intensity of 3.3 mW/cm$^2$ (sample No's. 6 and 7), still showed CPE in cell culture and resulted in virus titers of 8.2, 8.6 and 8.7 log $TCID_{50}$/ml, respectively. After 10 minutes of irradiation, all safety tests were negative.

UV-irradiation at intensities of both 2.1 mW/cm$^2$ and 3.3 mW/cm$^2$ for more than 10 minutes inactivated RRV preparations completely. Antigenicity, as shown in HA- and EIA-Tests, remained undamaged at both irradiation intensities for 15 minutes. After 30 minutes, the antigenicity was affected.

TABLE 8

Transfection and Infection Experiments with RRV RNA

| | | | RNA-Transfection (DMRIE-C) | | | | RNA-Infection | | |
|---|---|---|---|---|---|---|---|---|---|
| | | | C6-36 | | Vero | | C6-36 | Vero | |
| No | Sample | infect. PA* | log $TCID_{50}$ | HA | log $TCID_{50}$ | HA | log $TCID_{50}$ | log $TCID_{50}$ | HA |
| 1 | RNA-1 | 1 × $10^8$ | 7.4 | neg | 7.1 | 128 | 0.2 | 6.8 | 128 |
| | | 1 × $10^7$ | 5.5 | neg | 7.1 | 64 | 0.2 | neg | n.d. |
| | | 1 × $10^6$ | 7.6 | neg | 7.2 | 128 | 0.2 | neg | n.d. |
| | | 1 × $10^5$ | 5.2 | neg | 5.6 | 128 | | | |
| | | 1 × $10^4$ | 0.2 | neg | 0.2 | neg | | | |
| 2 | RNA-1 | 1 × $10^8$ | | | | | 0.2 | 0.2 | n.d. |
| 3 | RNA-1 | 1 × $10^8$ | 7.5 | n.d. | 4.6 | n.d. | 1.6 | 0.2 | n.d. |
| 4 | RNA-2 | 1 × $10^8$ | 7.2 | n.d. | 4.2 | n.d. | 8.4 | 6.6 | n.d. |
| | RNA-2 | 1 × $10^7$ | 7.0 | n.d. | 5.0 | n.d. | | | |
| 5 | RNA-2 | 1 × $10^8$ | | | | | 0.2 | 0.2 | n.d. |

*PA: infectious particle equivalents
n.d.: not done

TABLE 9

UV Inactivation of Infectious Virus.

| No | Sample | Treatment | Time (seconds) | $TCID_{50}$/ml | HA | EIA | UV-Intensity mW/$cm^2$ | UV Total mJ/$cm^2$ | Safety C6-36 $TCID_{50}$/ml |
|---|---|---|---|---|---|---|---|---|---|
| 1. | RRV PV/Sp5/57/4/98 | starting material | — | 7.4 | 9 | 640 | — | 0 | n.d. |
| 2. | RRV PV/Sp5/57/4/98 | 4 ml, 5 cm, 30 s | 30 | 4.4 | 9 | 640 | 2.1 | 63 | n.d. |
| 3. | RRV PV/Sp5/57/4/98 | 4 ml, 5 cm, 60 s | 60 | 3.7 | 9 | 640 | 2.1 | 126 | n.d. |
| 4. | RRV PV/Sp5/57/4/98 | 4 ml, 5 cm, 90 s | 90 | 1.7 | 9 | 640 | 2.1 | 189 | n.d. |
| 5. | RRV PV/Sp5/57/4/98 | 4 ml, 5 cm, 2 min | 120 | 1.8 | 9 | 640 | 2.1 | 252 | n.d. |
| 6. | RRV PV/Sp5/57/4/98 | 4 ml, 5 cm, 3 min | 180 | 3.2 | 9 | 1280 | 2.1 | 378 | +(8.2) |
| 7. | RRV PV/Sp5/57/4/98 | 4 ml, 5 cm, 5 min | 300 | 1.5 | 9 | 1280 | 2.1 | 630 | +(8.6) |
| 8. | RRV PV/Sp5/57/4/98 | 4 ml, 5 cm, 10 min | 600 | 1.5 | 9 | 1280 | 2.1 | 1260 | −(0.2) |
| 9. | RRV PV/Sp5/57/4/98 | 4 ml, 5 cm, 15 min | 900 | 1.5 | 9 | 640 | 2.1 | 1890 | −(0.2) |
| 10. | RRV PV/Sp5/57/4/98 | 4 ml, 5 cm, 30 min | 1800 | 1.5 | 7 | 320 | 2.1 | 3780 | −(0.2) |
| 11. | RRV PV/Sp5/57/4/98 | 4 ml, 3 cm, 30 s | 30 | 3.8 | 9 | 640 | 3.3 | 99 | n.d. |
| 12. | RRV PV/Sp5/57/4/98 | 4 ml, 3 cm, 60 s | 60 | 3.0 | 9 | 640 | 3.3 | 198 | n.d. |
| 13. | RRV PV/Sp5/57/4/98 | 4 ml, 3 cm, 90 s | 90 | 1.7 | 9 | 640 | 3.3 | 297 | n.d. |
| 14. | RRV PV/Sp5/57/4/98 | 4 ml, 3 cm, 2 min | 120 | 2.2 | 9 | 640 | 3.3 | 396 | +(8.2) |
| 15. | RRV PV/Sp5/57/4/98 | 4 ml, 3 cm, 3 min | 180 | 1.6 | 8 | 640 | 3.3 | 594 | +(8.6) |
| 16. | RRV PV/Sp5/57/4/98 | 4 ml, 3 cm, 5 min | 300 | 1.5 | 8 | 1280 | 3.3 | 990 | +(8.7) |
| 17. | RRV PV/Sp5/57/4/98 | 4 ml, 3 cm, 10 min | 600 | 1.5 | 8 | 640 | 3.3 | 1980 | −(0.2) |
| 18. | RRV PV/Sp5/57/4/98 | 4 ml, 3 cm, 15 min | 900 | 1.5 | 7 | 640 | 3.3 | 2970 | −(0.2) |
| 19. | RRV PV/Sp5/57/4/98 | 4 ml, 3 cm, 30 min | 1800 | 1.5 | 2 | 160 | 3.3 | 5940 | −(0.2) |
| 20. | positive control | | — | 7.2 | 9 | — | — | — | n.d. |

(D) UV-Inactivation of a Formalin Inactivated 1200 Liter Fermenter Harvest

An aliquot of a formalin treated 1200 liter fermenter virus harvest was UV-irradiated with 3 cycles at a flow rate of 300 l/h, 3 cycles at 150 l/h and 3 cycles at 75 l/h. A second aliquot of a formalin treated 1200 liter fermenter virus harvest was UV-irradiated with 10 cycles at a flow rate of 300 l/h, but this time after diafiltration, to remove high concentrations of small remaining proteins. HA-titers, antigen-EIA-titers, virus titers and safety (CPE) were determined after each run (Table 10).

Virus titers in the first experiment (without diafiltration) dropped after 1 cycle of UV-irradiation at a flow velocity 150 l/h from 6.13 log $TCID_{50}$/ml below the detection limit. Safety tests also showed no CPE. However, after 3 cycles of UV-irradiation at a flow rate 150 l/h, safety tests in cell culture showed positive results and were also positive in virus titration (6.7 log $TCID_{50}$/ml). 3 cycles of UV-irradiation at a flow rate 75 l/h remained negative in both virus titration and safety tests. In the second experiment safety tests and virus titration remained negative after 5 and more irradiation cycles. In the first experiment all irradiation doses did not influence HA- and EIA-titers with 11 and 1:320, respectively. In the second experiment all HA- and EIA-titers were 10 and 1:320, respectively, with the exception of 6 irradiation cycles, which resulted in an EIA-titer of 1:640.

Double inactivation of a fermenter harvest of RRV with formalin and five or more cycles of UV irradiation at a flow rate of 300 l/h is sufficient to completely destroy infectivity without damaging antigenicity.

TABLE 10

UV Inactivation of a RRV 1200 Liter Fermenter Harvest.

| Sample | HA-Titer | AG-EIA-Titer | $TCID_{50}$(after C6-36 Passage) | Safety Final Readout/CPE |
|---|---|---|---|---|
| RRV F07-31 Harvest + Formaldehyd starting material | 11 | 1:320 | 6.13 | ++++ |
| RRV F07-31 Ultrafiltrate | 4 | 1:80 | 7.04 | +−−− |
| RRV F07-31 Diafiltrate starting material | 11 | 1:320 | 5.95 | ++++ |
| RRV F07-31 Harvest + Formalin 1x UV 300 l/h | 11 | 1:320 | 6.29 | ++++ |
| RRV F07-31 Harvest + Formalin 2x UV 300 l/h | 11 | 1:320 | 5.71 | ++++ |
| RRV F07-31 Harvest + Formalin 3x UV 300 l/h | 11 | 1:320 | 6.31 | ++++ |
| RRV F07-31 Harvest + Formalin 1x UV 150 l/h | 11 | 1:320 | 0.21 | −−−− |
| RRV F07-31 Harvest + Formalin 2x UV 150 l/h | 11 | 1:320 | 0.21 | −−−− |
| RRV F07-31 Harvest + Formalin 3x UV 150 l/h | 11 | 1:320 | 6.70 | ++++ |
| RRV F07-31 Harvest + Formalin 1x UV 75 l/h | 11 | 1:320 | 0.21 | −−−− |
| RRV F07-31 Harvest + Formalin 2x UV 75 l/h | 11 | 1:320 | 0.21 | −−−− |
| RRV F07-31 Harvest + Formalin 3x UV 75 l/h | 11 | 1:320 | 0.21 | −−−− |
| RRV F07-31 Harvest + Formalin Diafiltrated 1x UV 300 l/h | 10 | 1:320 | 6.71 | ++++ |
| RRV F07-31 Harvest + Formalin Diafiltrated 2x UV 300 l/h | 10 | 1:320 | 6.71 | ++++ |
| RRV F07-31 Harvest + Formalin Diafiltrated 3x UV 300 l/h | 10 | 1:320 | 6.82 | ++++ |
| RRV F07-31 Harvest + Formalin Diafiltrated 4x UV 300 l/h | 10 | 1:320 | 2.82 | +−−− |
| RRV F07-31 Harvest + Formalin Diafiltrated 5x UV 300 l/h | 10 | 1:320 | 0.21 | −−−− |
| RRV F07-31 Harvest + Formalin Diafiltrated 6x UV 300 l/h | 10 | 1:640 | 0.21 | −−−− |
| RRV F07-31 Harvest + Formalin Diafiltrated 7x UV 300 l/h | 10 | 1:320 | 0.21 | −−−− |
| RRV F07-31 Harvest + Formalin Diafiltrated 8x UV 300 l/h | 10 | 1:320 | 0.21 | −−−− |
| RRV F07-31 Harvest + Formalin Diafiltrated 9x UV 300 l/h | 10 | 1:320 | 0.21 | −−−− |
| RRV F07-31 Harvest + Formalin Diafiltrated 10x UV 300 l/h | 10 | 1:320 | 0.21 | −−−− |

(E) Efficacy of Double Inactivated RRV Candidate Vaccine Preparations Effective Dose ($ED_{50}$), Protective Dose ($PD_{50}$) and ELISA Titers in Immunized Mice A formalin-inactivated and a double-inactivated (formalin+UV-irradiation) RRV candidate vaccine was adjusted to 10 μg per dose, and then diluted in 4 fold steps. Each dilution was injected into a group of 10 mice. After 3 weeks the mice were boostered with the corresponding amount of the vaccine. Blood samples were drawn at week 3, before the booster, and at week 6, 3 weeks after the booster. The sera were analyzed by a RRV antibody ELISA. The effective dose 50 ($ED_{50}$), this is the antigen dose which is sufficient to induce seroconversion in 50% of the immunized mice, was then calculated.

At week 3, before the booster, the $ED_{50}$ of the formalin-inactivated group was 635 ng and of the group with the formalin and UV double inactivation 202 ng. After the booster, the $ED_{50}$ values were 33 ng and 10 ng, respectively. The analysis of the ELISA titers, however, demonstrated that the group with the double inactivation had even higher antibody titers, for example at week 3, 9 mice with an ELISA titer of 1,000 against 16 mice with 1,000 in the double inactivation group, and no mouse with 10,000 in the formalin group against 4 mice with 10,000 in the double inactivation group. After the booster, again the titers of the double inactivation group were higher: 8 mice in the formalin group compared to 11 mice in the double inactivation group with 100,000, and additional 4 mice with an ELISA titer of 1 million in the double inactivation group (Table 11).

At week 6, 3 weeks after the booster, the mice were infected intravenously with $10^6$ $TCID_{50}$/ml (tissue culture infective dose 50) of live Ross River Virus (strain T48). At day 1, 2, 3 and 4 p.i. blood samples were taken and the $TCID_{50}$ of the serum was subsequently determined. The protective dose 50 ($PD_{50}$), this is the antigen dose at which 50% of the infected mice showed no viremia, was calculated. The $PD_{50}$ of 78 ng was identical for both antigen preparations, the formalin-inactivated as well as the double-inactivated (formalin+UV-irradiation) antigen.

TABLE 11

Effective Dose ($ED_{50}$), Protective Dose ($PD_{50}$) and ELISA Titers in Immunized Mice.

| | $ED_{50}$ | | |
|---|---|---|---|
| Inactivation | Week 3 | Week 6 (Booster) | $PD_{50}$ Week 6 |
| Formalin | 635 ng | 33 ng | 78 ng |
| Formalin + UV | 202 ng | 10 ng | 78 ng |

ELISA-Titer

| Week | Inact. | $<10^1$ | $10^1$ | $10^2$ | $10^3$ | $10^4$ | $10^5$ | $10^6$ | $10^7$ | $10^8$ | N |
|---|---|---|---|---|---|---|---|---|---|---|---|
| 3 | Form. | 35 | 8 | 8 | 9 | 0 | 0 | 0 | 0 | 0 | 60 |
| | Form. + UV | 27 | 7 | 6 | 16 | 4 | 0 | 0 | 0 | 0 | 60 |
| 6 | Form. | 14 | 7 | 5 | 15 | 11 | 8 | 0 | 0 | 0 | 60 |
| | Form. + UV | 8 | 7 | 9 | 7 | 14 | 11 | 4 | 0 | 0 | 60 |

The residual infectivity found primarily in the very sensitive C6-36 cell line after formalin treatment alone, is most probably caused by infectious RRV RNA. The introduction of a second additional virus inactivation step (UV-irradiation), affecting the genome of the virus after the formalin treatment, resulted in fully inactivated and safe RRV candidate vaccine preparations without affecting immunogenicity and efficacy in a mouse model.

We claim:

1. A method for inactivating an enveloped virus contained in a sample for producing a vaccine, comprising the steps of (i) treating the sample with an effective concentration of formalin, and (ii) subjecting the sample to an effective dose of UV light in a flow-through apparatus, wherein step (i) is performed prior to step (ii) or vice versa, and wherein the enveloped virus is wholly inactivated, thereby being suitable for use in producing the vaccine.

2. The method of claim 1, wherein the virus titre reduction due to the inactivation of the virus in the sample is at least about $1\times10^5$.

3. The method of claim 1, wherein the virus titre reduction due to the inactivation of the virus in the sample is at least about $1\times10^7$.

4. The method of claim 1, wherein the virus titre reduction due to the inactivation of the virus in the sample is at least about $1\times10^{10}$.

5. The method of claim 1, wherein the virus titre reduction due to the inactivation of the virus in the sample is at least about $1\times10^{14}$.

6. The method of claim 1, wherein the step of treating the sample with an effective concentration of formalin is carried out for about 12 to about 96 hours.

7. The method of claim 1, wherein the effective concentration of formalin is about 0.01 to about 0.1%.

8. The method of claim 1, wherein the UV light is UVC with a wavelength of about 100 to about 280 nm.

9. The method of claim 1, wherein the dose of UV light is about 5 to about 200 mJ/cm2.

10. The method of claim 1, wherein the contact time of the sample with the UV light is about 1 to about 20 seconds.

11. The method of claim 1, wherein the flow rate in the flow-through apparatus is from about 50 liters per hour to about 1000 liters per hour.

12. The method of claim 1, wherein the flow-through apparatus contains a thin layer chamber.

13. The method of claim 12, wherein the thin layer of the thin layer chamber has a thickness of about 1 mm.

14. The method of claim 1, wherein the step of subjecting the sample to an effective dose of UV light in a flow-through apparatus is repeated for about 2 to about 10 times.

15. The method of claim 1, wherein the sample is selected from the group consisting of biological fluids, or solutions originating from a cell culture process.

16. The method of claim 1 further comprising the step of subjecting the sample to a purification step to remove residual formalin in the sample.

17. The method of claim 1 further comprising purifying the inactivated virus in the sample to pharmaceutical purity, and formulating the purified inactivated virus into a pharmaceutical composition for use as a vaccine.

18. The method of claim 1, further comprising a test subsequent to steps (i) and (ii) to determine the residual infectivity of the inactivated virus, the test comprising the steps of a) inoculating a mammalian cell culture with the inactivated enveloped virus b) incubating the cell culture, c) harvesting the cell culture and inoculating a second mammalian cell culture with the harvest, d) incubating the second mammalian cell culture, e) harvesting the second mammalian cell culture and testing the harvest for hemagglutinin activity, wherein the results from the test indicate that the enveloped virus is wholly inactivated, thereby being suitable for use in producing the vaccine.

19. The method of claim 18, wherein the mammalian cell culture is a VERO cell culture.

20. The method of claim 18, wherein the cell culture is incubated for about 7 days in step b) or d).

* * * * *